United States Patent
Gass (10) Patent No.: US 8,119,125 B2
(45) Date of Patent: Feb. 21, 2012

(54) COMPOSITIONS AND METHODS FOR ENHANCED GASTROINTESTINAL STABILITY OF OLIGOPEPTIDES AND POLYPEPTIDES

(75) Inventor: Jonathan David Gass, Mountain View, CA (US)

(73) Assignee: Alvine Pharmaceuticals, Inc., Palo Alto, CA (US)

( * ) Notice: Subject to any disclaimer, the term of this patent is extended or adjusted under 35 U.S.C. 154(b) by 782 days.

(21) Appl. No.: 12/089,705

(22) PCT Filed: Oct. 11, 2006

(86) PCT No.: PCT/US2006/040091
§ 371 (c)(1),
(2), (4) Date: Sep. 2, 2008

(87) PCT Pub. No.: WO2007/044906
PCT Pub. Date: Apr. 19, 2007

(65) Prior Publication Data
US 2008/0311161 A1    Dec. 18, 2008

Related U.S. Application Data

(60) Provisional application No. 60/725,733, filed on Oct. 11, 2005.

(51) Int. Cl.
*A61K 38/48* (2006.01)
*A61K 31/74* (2006.01)
(52) U.S. Cl. .......... 424/94.63; 424/78.1; 424/417; 424/483
(58) Field of Classification Search .......... 424/78.1, 424/94.63, 417, 483
See application file for complete search history.

(56) References Cited

U.S. PATENT DOCUMENTS

| 4,600,578 | A | * | 7/1986 | Pircio et al. ............... 424/78.01 |
| 7,303,871 | B2 | | 12/2007 | Hausch et al. |
| 7,320,788 | B2 | | 1/2008 | Shan et al. |
| 2003/0124088 | A1 | * | 7/2003 | Masuda et al. ............. 424/78.31 |
| 2003/0215438 | A1 | | 11/2003 | Hausch et al. |
| 2003/0219400 | A1 | * | 11/2003 | Shoemaker et al. ......... 424/78.1 |
| 2005/0008638 | A1 | | 1/2005 | Lu et al. |
| 2006/0002917 | A1 | | 1/2006 | Piper et al. |
| 2008/0095710 | A1 | | 4/2008 | Shan et al. |
| 2008/0145356 | A1 | | 6/2008 | Hausch et al. |
| 2008/0193436 | A1 | | 8/2008 | Shan et al. |
| 2008/0213245 | A1 | | 9/2008 | Hausch et al. |
| 2008/0213427 | A1 | | 9/2008 | Hausch et al. |
| 2008/0213822 | A1 | | 9/2008 | Hausch et al. |
| 2008/0299108 | A1 | | 12/2008 | Khosla et al. |

OTHER PUBLICATIONS

Bai. Malabsorption Syndromes. Digestion. 1998;58:530-546.*
Shan et al. Comparative biochemical analysis of three bacterial prolyl endopeptidases: implications for coeliac sprue. Biochem. J. (2004) 383:p. 311-318.*
Hausch; et al., "Enzyme Treatment of Foodstuffs for Celiac Sprue", U.S. Appl. No. 11/927,536, filed Oct. 29, 2007.
Khosla; et al., "Combination Enzyme Therapy for Gastric Digestion of Dietary Gluten in Celiac Sprue Patients", U.S. Appl. No. 12/330,402, filed Dec. 8, 2008.

* cited by examiner

*Primary Examiner* — Taeyoon Kim
(74) *Attorney, Agent, or Firm* — Bozicevic, Field & Francis LLP; Pamela J. Sherwood (57) ABSTRACT

Methods and compositions are provided for stabilizing polypeptides for oral administration, particularly where enteric delivery is desirable. By administering the polypeptides with a bile sequestering agent, the stability of the polypeptide can be increased. Pharmaceutical formulations for this purpose are provided.

6 Claims, 3 Drawing Sheets

COMPOSITIONS AND METHODS FOR ENHANCED GASTROINTESTINAL STABILITY OF OLIGOPEPTIDES AND POLYPEPTIDES

BACKGROUND OF THE INVENTION

The invention relates to biologically active peptides and polypeptides and methods for administering them orally. Advances in the fields of genetic engineering, biotechnology, and peptide chemistry have led to the development of ever increasing number of proteins and peptides that have potential utility as pharmaceutical agents. The development of methods for administering these new pharmaceutical agents is thus of ever increasing importance. In particular, the local or systemic administration of biologically active substances, such as peptides and proteins, is a current concern.

The delivery of peptides and proteins can be complicated, as peptides and proteins are subject to degradation in many physiological environments. For example, while oral delivery is often desirable, it exposes polypeptides to harsh conditions. Enteric coated compositions are useful in overcoming the degradation of peptides and proteins in the stomach due to acidic conditions. Enteric coating materials are generally anionic polymers that are insoluble in buffer solutions below about pH 5 and in gastric fluid but soluble in neutral to weakly alkaline buffer solutions above about pH 5.5 and in intestinal fluid. Release of the medicament within the enteric coating may occur by dissolution, leaching, erosion, rupture, diffusion, or similar actions, depending upon such factors as the nature and thickness of the coating material. Alternatively, some polypeptides are naturally resistant to acidic conditions, and can be delivered to the intestines in the absence of such coatings.

However, once reaching the intestines, certain peptides and polypeptides may be susceptible to proteolytic digestion by enzymes such as trypsin and chymotrypsin, thereby limiting the bioavailability and half-life of the drug.

Improved formulations and methods of delivery that enhance the stability of therapeutic polypeptides in the intestines are of interest for clinical purposes. The present invention addresses this need.

SUMMARY OF THE INVENTION

Methods and compositions are provided for stabilizing peptides and oligopeptides or polypeptides for oral administration, including but not limited to oral administration for enteric delivery. The presence of bile salts may increase the susceptibility of certain peptides and polypeptides to proteolytic degradation. By administering the peptides or polypeptides with a bile sequestering agent, the stability of the polypeptide can be increased. Pharmaceutical formulations for this purpose are provided and contain an active pharmaceutical ingredient (API) selected from the group consisting of a peptide, a polypeptide, and peptidomimetic analogs of either; and a bile sequestering agent, optionally with other ingredients, such as pharmaceutically acceptable carriers, excipients, compacting agents, and the like.

In some embodiments, the invention provides a pharmaceutical formulation of a peptide or polypeptide in a co-formulation with a bile sequestering agent. Such formulations include, without limitation, capsules, pills, and the like, which optionally comprise an enteric coating; as well as sachets, powders, and the like. In other embodiments of the invention, the polypeptide is separately formulated from the bile sequestering agent, and the two separate formulations are administered simultaneously or contemporaneously with one another.

In some embodiments of the invention, the API is a polypeptide. In one embodiment of the invention the API is a polypeptide glutenase. In one embodiment of the invention, the glutenase is a bacterial prolyl endopeptidase (PEP) or variant derived therefrom. In various embodiments of the invention, the PEP is a PEP from *Flavobacterium meningosepticum* (FM), *Sphingomonas capsulate* (SC), or *Myxococcus xanthus* (MX), or is a variant of one of such PEPs, or is a mixture of one of the foregoing, or is one of the foregoing in admixture with another protease, including but not limited to cysteine endoproteases, including but not limited to barley cysteine endoprotease (EP-B). The FM, SC, and MX glutenase enzymes exhibit differences in activity profile with respect to chain length and subsite specificity. These enzymes and methods for their use in the in vivo detoxification of gluten are described in PCT patent publication Nos. 2005/107786 and 2003/0215438. In one embodiment of the invention, one or more of the FM, SC, and MX PEPs are used to decrease the levels of toxic gluten oligopeptides in foodstuffs by oral administration to a human consuming such foodstuffs.

In another aspect, the invention provides pharmaceutical formulations containing one or more glutenases, a bile sequestering agent, and a pharmaceutically acceptable carrier. Such formulations include formulations in which the glutenase is contained within an enteric coating that allows delivery of the active agent to the intestine and formulations in which the active agents are stabilized to resist digestion in acidic stomach conditions. The formulation may comprise one or more glutenases or a mixture or "cocktail" of agents having different activities. Depending upon their pH optima, glutenases can hydrolyze gluten or gluten peptides in the stomach (i.e. at strongly acidic pH values) or in the small intestine (i.e. mildly acidic pH values).

In another aspect, the invention provides methods for treating Celiac Sprue by administering a glutenase in combination with a bile-sequestering agent. In one embodiment, the glutenase and bile-sequestering agent are administered orally. In one embodiment, the glutenase and bile-sequestering agent are admixed prior to administration. In one embodiment, at least 10 mg of glutenase are administered. In other embodiments, at least 100 mg, 250 mg, 500 mg or more of glutenase are administered. In one embodiment, sufficient glutenase is administered to hydrolyze at least 1 g of gluten per unit dose. In other embodiments, sufficient glutenase is administered to hydrolyze 5 g, 10 g, 20 g or more gluten per unit dose. In one embodiment, at least 0.5 g bile sequestering agent is administered. In other embodiments, 1 g, 3 g, 10 g or more of bile sequestering agent is administered.

In another aspect, the invention provides unit dose forms of a glutenase admixed with a bile-sequestering agent suitable for oral administration to a human. In one embodiment, at least 10 mg of glutenase are contained in the unit dose. In other embodiments, at least 100 mg, 250 mg, 500 mg or more of glutenase are administered. In one embodiment, sufficient glutenase to hydrolyze at least 1 g of gluten is contained in each unit dose. In other embodiments, sufficient glutenase is administered to hydrolyze 5 g, 10 g, 20 g or more gluten per unit dose. In one embodiment, at least 0.5 g bile sequestering agent is admixed with said glutenase. In other embodiments, 1 g, 3 g, 10 g or more of bile sequestering agent is admixed with said glutenase.

These and other aspects and embodiments of the invention are described in more detail below.

DETAILED DESCRIPTION OF THE EMBODIMENTS

Peptides and polypeptides delivered orally are susceptible to various degradative conditions, including proteolytic digestion in the presence of enzymes and bile salts in the intestine. The present invention arises in part out of the discoveries that certain peptides and polypeptides are susceptible to such degradation and that those peptides and polypeptides can be made resistant to such enzymes and salts by the co-administration of a bile salt sequestering agent. Pharmaceutical formulations for this purpose, and new therapeutic methods made possible by them and/or representing improvements over known methods are provided.

The present invention relates generally to methods and reagents useful in formulating peptides and polypeptides for oral administration. In one important embodiment, the invention provides oral formulations of peptides and polypeptides, and methods for making and using them, suitable for enteric delivery. The present invention also relates generally to the treatment of diseases and conditions by the oral administration of a peptide or polypeptide that, in its native state, is susceptible to degradation or other inactivation by bile salts. Thus, the practice of the present invention may employ conventional techniques of molecular biology (including recombinant techniques), microbiology, cell biology, biochemistry, peptide chemistry and immunology within the scope of those of skill in the art. Such techniques are described in the scientific literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

Bile salts are steroid compounds (chenodeoxycholic, deoxycholic and cholic acid), often conjugated with glycine and taurine, and act to some extent as a detergent, helping to emulsify fats, and thus aid in the absorption of fats in the small intestine. The two most prevalent bile salt compounds in the human gut are the salts of glycocholic acid and glycochenodeoxycholic acid. Bile salts combine with phospholipids to break down fat globules in the process of emulsification.

Bile acid sequestrants bind with cholesterol-containing bile acids in the intestines and are then eliminated in the stool. Cholestyramine, colestipol, and colesevelam are bile acid sequestrants that are commercially available, but a wide variety of bile acid sequestrants are known in the art and can be used in accordance with the methods and reagents of the invention. These sequestrants are also commercially available as powders or tablets. They are not absorbed from the gastrointestinal tract, and 30 years of experience with such sequestrants demonstrate that long-term use of them in humans is safe. In one embodiment, the present invention relates to pharmaceutical formulations and unit dose forms and methods of treating human disease in which the unit dose of bile acid sequestrant is usually at least about 0.5 grams, or at least about 1 gram, or at least about 3 grams, and usually not more than about 10 grams per unit dose. In one embodiment, the API is a glutenase and the unit dose of bile sequestrant is administered simultaneously or contemporaneously with the sequestrant at mealtime. In other embodiments in which the API may be a glutenase or any other therapeutic protein or peptide, the bile sequestrant is administered in unit dose form daily, twice daily, or as needed depending on the API and delivery regimen.

Therapeutic peptides and polypeptides are the API in the formulations of the invention. Peptides and proteins for which oral delivery is desirable include, e.g., insulin, antibodies and immunoglobulin, growth factors, clotting factors, pancreatic enzymes, and the like. A review of polypeptides of current interest is Hamman et al. (2005) BioDrugs 19(3):165-77, herein incorporated by reference.

Therapeutic polypeptides of particular interest include glutenases. For example, see US patent application publication Nos. US-2003-0215438-A1 and US-2005-0249719 and PCT patent publication No. 2005/107786, each herein specifically incorporated by reference, for glutenases of interest. As used herein, the term "glutenase" refers to an enzyme useful in the methods of the present invention that is capable, alone or in combination with endogenous or exogenously added enzymes, of cleaving oligopeptides of gluten proteins of wheat, barley, oats and rye that are toxic to Celiac Sprue patients into non-toxic or less toxic (to Celiac Sprue patients) fragments. Gluten is the protein fraction in cereal dough, which can be subdivided into glutenins and prolamines, which are subclassified as gliadins, secalins, hordeins, and avenins, and which can be isolated from wheat, rye, barley and oats. For further discussion of gluten proteins, see the review by Wieser (1996) Acta Paediatr Suppl. 412:3-9, incorporated herein by reference.

As used herein, the term "glutenase" refers to an enzyme useful in the methods of the present invention that is capable, alone or in combination with endogenous or exogenously added enzymes, of cleaving toxic oligopeptides of gluten proteins of wheat, barley, oats and rye into non-toxic fragments. For example, see US patent application publication Nos. US-2003-0215438-A1 US-2005-0249719-A1 and PCT patent publication 2005/107786, each herein specifically incorporated by reference. Gluten is the protein fraction in cereal dough, which can be subdivided into glutenins and prolamines, which are subclassified as gliadins, secalins, hordeins, and avenins from wheat, rye, barley and oats, respectively. For further discussion of gluten proteins, see the review by Wieser (1996) Acta Paediatr Suppl. 412:3-9, incorporated herein by reference.

In one embodiment, the term "glutenase" as used herein refers to a protease or a peptidase enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "protease" or "peptidase" can refer to a glutenase and as used herein describe a protein or fragment thereof with the capability of cleaving peptide bonds, where the scissile peptide bond may either be terminal or internal in oligopeptides or larger proteins. Prolyl-specific peptidases are glutenases useful in the practice of the present invention.

Glutenases of the invention include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. capsulata* (Genbank accession number AB010298), DCP I from rabbit (Genbank accession number X62551), PEP from *Aspergillus niger*, DPP IV from *Aspergillus fumigatus* (Genbank accession number U87950), and cysteine proteinase B from *Hordeum vulgare* (Genbank accession number JQ1110).

Each of the above proteases described herein can be engineered to improve desired properties such as enhanced specificity toward toxic gliadin sequences, improved tolerance for longer substrates, acid stability, pepsin resistance, resistance to proteolysis by the pancreatic enzymes and improved shelf-life. The desired property can be engineered via standard protein engineering methods.

In one embodiment of the present invention, the glutenase is a PEP. Homology-based identification (for example, by a PILEUP sequence analysis) of prolyl endopeptidases can be routinely performed by those of skill in the art upon contemplation of this disclosure to identify PEPs suitable for use in the methods of the present invention. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningoscepticum, Aspergillus niger, Aeromonas hydrophila, Aeromonas punctata, Novosphingobium capsulatum, Pyrococcus furiosus* and from mammalian sources are biochemically characterized PEPs. Others such as the *Nostoc* and *Arabidopsis* enzymes are likely to be PEPs but have not been fully characterized to date. Homologs of the enzymes of interest may be found in publicly available sequence databases, and the methods of the invention include such homologs. Candidate enzymes are expressed using standard heterologous expression technologies, and their properties are evaluated using the assays described herein.

In one embodiment of the invention, the glutenase is *Flavobacterium meningosepticum* PEP (Genbank ID # D10980). Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme. A variety of assays have verified the therapeutic utility of this PEP. In vitro, this enzyme has been shown to rapidly cleave several toxic gluten peptides, including the highly inflammatory 33-mer, (SEQ ID NO:12) LQLQPF-PQPQLPYPQPQLPYPQPQLPYPQPQPF. In vivo it acts synergistically with the peptidases of the intestinal brush border membrane so as to rapidly detoxify these peptides, as well as gluten that has been pre-treated with gastric and pancreatic proteases. It has broad chain length specificity, making it especially well suited for the breakdown of long proline-rich peptides released into the duodenum from the stomach. The enzyme has a pH optimum around pH 7, and has high specific activity under conditions that mimic the weakly acidic environment of the upper small intestine. *Flavobacterium* PEP can cleave all T cell epitopes in gluten that have been tested to date. It has particular preference for the immunodominant epitopes found in alpha-gliadin. When grocery-store gluten is treated with this PEP, a rapid decrease in its antigenicity can be observed, as judged by LC-MS analysis and testing against polyclonal T cell lines derived from small intestinal biopsies from Celiac Sprue patients. The denatured protein is non-allergenic in rodents, rabbits and humans. It is relatively stable toward destruction by pancreatic proteases, an important feature since under physiological conditions it will be expected to act in concert with those enzymes.

Another enzyme of interest is *Myxococcus xanthus* PEP (Genbank ID# AF127082), which is provided in PEGylated form by the present invention. This enzyme possesses many of the advantages of the *Flavobacterium* PEP. It can cleave the 33-mer into small non-toxic peptides. Whereas the *Flavobacterium* enzyme appears to have a relatively strict preference for PQ bonds in gliadin peptides, the *Myxococcus* enzyme can cleave at PQ, PY and PF bonds, a feature that allows it to proteolyze a broader range of gluten epitopes. Compared to the *Flavobacterium* enzyme, it has equivalent stability toward the pancreatic proteases and superior stability toward acidic environments. The *Myxococcus* enzyme is well expressed in *E. coli*, making it feasible to produce this enzyme cost-effectively.

Another enzyme of interest is *Sphingomonas capsulata* PEP (Genbank ID# AB010298), which is provided in PEGylated form by the present invention. This enzyme is comparable to the *Flavobacterium* and *Myxococcus* enzymes. It has broader sequence and pH specificity than either the *Flavobacterium* or the *Myxococcus* PEP, and may therefore be able to destroy the widest range of antigenic epitopes, while also being active in the stomach. Like the *Myxococcus* enzyme, it is also well expressed in *E. coli*.

Another enzyme of interest is *Lactobacillus helveticus* PEP (Genbank ID# 321529), which is provided in PEGylated form by the present invention. Unlike the above PEPs, this PEP is a zinc enzyme. It can efficiently proteolyze long peptide substrates such as the case in peptides (SEQ ID NO:28) YQEPVLGPVRGPFPIIV and (SEQ ID NO:29) RPKH-PIKHQ. Proteolysis occurs at all PV and PI subsites, suggesting the PEP prefers hydrophobic residues at the S1' position, as are frequently found in gluten. Because the producer strain of *L. helveticus* CNRZ32 is commonly used in cheesemaking, this enzyme has desirable properties as a food-grade enzyme.

Another enzyme of interest is *Penicillium citrinum* PEP (Genbank ID# D25535), which is provided in PEGylated form by the present invention. This enzyme has been shown to possess PEP activity based on its ability to cleave a number of Pro-Xaa bonds effectively in peptides such as dynorphin A and substance P. The putative metalloprotease has the advantages of small size and a pH profile that renders it suitable to working in concert with the pancreatic enzymes in the duodenum. As such, it can be used to detoxify gluten for the treatment of Celiac Sprue.

Other than proline, glutamine residues are also highly prevalent in gluten proteins. The toxicity of gluten in Celiac Sprue has been directly correlated to the presence of specific Gin residues. Therefore, glutamine-specific proteases are also beneficial for the treatment of Celiac Sprue. Because oats contain proteins that are rich in glutamine but not especially rich in proline residues, an additional benefit of a glutamine-specific protease is the improvement of oat tolerance in those celiac patients who show mild oat-intolerance. An example of such a protease is the above-mentioned cysteine endoproteinase from *Hordeum vulgare* endoprotease (Genbank accession U19384), and the present invention provides this enzyme in PEGylated form. This enzyme cleaves gluten proteins rapidly with a distinct preference for post-Gln cleavage. The enzyme is active under acidic conditions, and is useful as an orally administered dietary supplement. A gluten-containing diet may be supplemented with orally administered proEPB2, resulting in effective degradation of immunogenic gluten peptides in the acidic stomach, before these peptides enter the intestine and are presented to the immune system. The proEPB2 is the zymogen form of the *Hordeum vulgare* EPB2 protease; the acidic conditions of the stomach activate the zymogen; the present invention provides PEGylated forms of both the proEPB2 and EPB2 enzymes. Proteins with high sequence similarity to this enzyme are also of interest and PEGylated versions of them are provided by the present invention. An advantage of these enzymes is that they are considered as safe for human oral consumption, due to their presence in dietary gluten from barley.

Intestinal dipeptidyl peptidase IV and dipeptidyl carboxypeptidase I are the rate-limiting enzymes in the breakdown of toxic gliadin peptides from gluten. These enzymes are bottlenecks in gluten digestion in the mammalian small intestine because (i) their specific activity is relatively low compared to other amino- and carboxy-peptidases in the intestinal brush border; and (ii) due to their strong sensitivity to substrate chain length, they cleave long immunotoxic peptides such as the 33-mer extremely slowly. Both these problems can be ameliorated through the administration of proline-specific amino- and carboxy-peptidases from other sources. For example the X-Pro dipeptidase from *Aspergillus oryzae* (GenBank ID# BD191984) and the carboxypeptidase from *Aspergillus saitoi* (GenBank ID# D25288) can improve gluten digestion in the Celiac intestine. PEGylated forms of these enzymes are provided by the present invention.

The glutenase proteins of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. Using synthesizers, one can readily substitute for the naturally occurring amino acids one or more unnatural amino acids. The particular sequence and the manner of preparation will be determined by convenience, economics, purity required, and the like. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

The glutenase proteins useful in the practice of the present invention may also be isolated and purified in accordance with conventional methods from recombinant production systems and from natural sources. Protease production can be achieved using established host-vector systems in organisms such as *E. coli, S. cerevisiae, P. pastoris, Lactobacilli, Bacilli* and *Aspergilli*. Integrative or self-replicative vectors may be used for this purpose. In some of these hosts, the protease is expressed as an intracellular protein and subsequently purified, whereas in other hosts the enzyme is secreted into the extracellular medium. Purification of the protein can be performed by a combination of ion exchange chromatography, Ni-affinity chromatography (or some alternative chromatographic procedure), hydrophobic interaction chromatography, and/or other purification techniques. Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In another embodiment of the invention, one or more of these proteases or another protease active in the small intestine is co-administered with another PEP, including but not limited to the PEP derived from *Aspergillus niger* described in US patent application publication No. 2004-0241664-A1, or other protease, such as the barley cysteine proteinase B, that is active in the stomach.

As used herein, compounds that are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the glutenases of the invention, such as bile sequestrants and pharmaceutical carriers, compacting agents, and other sequestrants can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley Interscience, New York, 1992. Specific and analogous reactants may also be identified through the indices of known chemicals prepared by the Chemical Abstract Service of the American Chemical Society, which are available in most public and university libraries, as well as through on line databases (the American Chemical Society, Washington, D.C., www.acs.org may be contacted for more details). Chemicals that are known but not commercially available in catalogs may be prepared by custom chemical synthesis houses; many of the standard chemical supply houses (e.g., those listed above) provide custom synthesis services.

Formulations

The peptide or polypeptide API and bile sequestering agent can be incorporated into a variety of formulations for therapeutic administration in accordance with the present invention. For example, a simple formulation incorporating the bile sequestering agent as an excipient in the lyophilization and formulation process with a polypeptide is useful for some applications. The sequestering agent and polypeptide are combined in solution, then frozen and lyophilized. The resulting powder can be formulated in a capsule, sachet, pill, and the like, and may further be formulated to comprise an enteric coating. Alternatively, the sequestering agent can be added after the lyophilization process. In this process, the resin is blended into the API formulation, which may be a lyophilized product.

In one aspect, the agents are formulated into pharmaceutical compositions by combination with appropriate, pharmaceutically acceptable carriers or diluents, and are formulated into preparations in solid, semi-solid, or liquid forms, such as tablets, capsules, powders, granules, solutions, gels, and microspheres. As such, administration of the polypeptide and/or other compounds can be achieved by oral administration.

In pharmaceutical dosage forms, the peptide and polypeptide and/or other compounds may be administered in the form of their pharmaceutically acceptable salts, or they may also be used alone or in appropriate association, as well as in combination, with other pharmaceutically active compounds. The agents may be combined, as previously described, to provide a cocktail of activities. The following methods and excipients are exemplary and are not to be construed as limiting the invention.

For oral preparations, the agents (therapeutic protein or peptide and bile sequestrant) can be used alone or in combination with appropriate additives to make tablets, powders, granules or capsules, for example, with conventional additives, such as lactose, mannitol, corn starch or potato starch; with binders, such as microcrystalline cellulose, cellulose derivatives, acacia, corn starch or gelatins; with disintegrants, such as corn starch, potato starch or croscarmellose sodium; with lubricants, such as talc or magnesium stearate; and if desired, with diluents, buffering agents, moistening agents, preservatives, colorants, and flavoring agents.

In one embodiment of the invention, the API is a glutenase, including but not limited to a PEP, and the oral formulations comprise enteric coatings, so that the API is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2 dimethylaminoethanol, 2 diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, a glutenase may be administered in dosages of 0.01 mg to 500 mg/kg body weight per day, e.g. about 20, 100, 250, 500 or more mg/day or about 0.5, 1, 1.5, or more g/day for an average person. A typical dose of glutenase in patients will be in at least about 1 mg/adult patient, more usually at least about 10 mg/adult patient; and usually at least about 50, 150, 250, 500 or more mg/adult patient; usually not more than about 5 g, not more than about 1 g, or not more than about 500 mg/adult patient. Efficient proteolysis of gluten in vivo for an adult may, depending on diet and other factors, require at least about 500 units of a therapeutically efficacious PEP, In some embodiments, low dose PEP, such as 1000 units, can be used. In other embodiments, such as for the rapid detoxification of 5-10 g ingested gluten, as much as 20,000-50,000 units may be provided in unit dose form. One unit is defined as the amount of enzyme required to hydrolyze 1 µmol Cbz-Gly-Pro-pNA (for PEP) or Cbz-Gly-Gln-pNA (for a glutamine-specific protease) per min under specified conditions. Most PEPs have specific activities in the range of 5-50 units/mg protein. For barley EP-B2 (whose specific activity is in the 1000 Units/mg range, as measured with Cbz-Phe-Arg-pNA), low dose glutenase may consist of 10,000-100,000 Units, whereas high-dose glutenase contains as much as 1,000,000 Units. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1, 0.5, 1, 10, 20, 100, 150, 250 or more mg. In combination therapy involving, for example, a PEP+DPP IV or PEP+DCP I or PEP+Barley EP-B2 endoproteinase, a comparable dose of the two enzymes may be given; however, the ratio will be influenced by the relative stability of the two enzymes toward gastric and duodenal inactivation. The anticipated doses of bile sequestrants are in the range of 0.5 g to 10 g or more.

Those of skill will readily appreciate that dose levels can vary as a function of the specific enzyme, the severity of the symptoms and the susceptibility of the subject to side effects. Some of the glutenases are more potent than others. Preferred dosages for a given enzyme are readily determinable by those of skill in the art by a variety of means. One means applicable to glutenases is to determine the amount of gluten a glutenase can digest by proteolytic action into non-toxic (to Celiac sprue patients) amino acids and short peptides under physiologic conditions (which may be replicated in in vitro, ex vivo, and in vivo model systems). Another means is to measure the physiological potency of a given compound.

The therapeutic effect can be measured in terms of clinical outcome or can be determined by immunological or biochemical tests. For example, in the treatment of Celiac sprue, suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease, e.g. as set forth in Pyle et al, *Clin. Gastroenterol. Hepatol.* 3, 679-686, 2005.

Various methods for administration may be employed, it being appreciated that the formulations of peptides and proteins provided by the present invention provide improved formulations for oral administration. For example, in the treatment of Celiac Sprue with a glutenase, the present invention provides unit dose forms of the glutenase suitable for administration with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semiweekly, or otherwise as needed to maintain an effective dosage level.

Cross-reference to related applications. The present application is related to the following co-pending patent application which is filed on the same date on which the present application is filed, and which is incorporated herein in its entirety by reference: International patent application Ser. No. PCT/US06/39714 entitled "Pegylated Glutenase Polypeptides" by Srebrenka Robic, which claims priority to US provisional application 60/726,130.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

EXAMPLE 1

Formulations and Associated Preparation Methods for PEP and Mixtures of PEP with Other Proteases Overcoming PEP Susceptibility to Gastric Conditions. PEP enzymes (*Flavobacterium meningosepticum*, FM, and *Myxococcus xanthus*, MX) have limited activity in the presence of gastric conditions of low pH (2) and pepsin exposure (Shan et al. Biochem J. 2004 Oct. 15; 383(Pt 2):311-8). An enteric coated formulation, prepared using Eudragit L100-55 or L30 D-55 enteric coat, provided by the present invention markedly improves the stability of these and other PEP enzymes under such conditions. Briefly, the PEP enzyme is lyophilized in the presence of 50 mM $Na_2HPO_4$ and 3% Sucrose to form a stable, dry powder. The powder is blended with various excipients, such as talc and microcrystalline cellulose. The powder blend can either be compacted manually into small granules (5-10 mg/granule) or encapsulated into a gelatin capsule. The granule or capsule is then coated with the Eudragit enteric coat using, for example, a hand held spraying device and an air dryer. The coated material has demonstrated resistance to simulated gastric conditions (pH 2 and 0.6 mg/ml pepsin), while still providing drug release at simulated intestinal conditions (pH 6 with various levels of trypsin and chymotrypsin) (see FIG. 1 for MX PEP). Such formulations provide distinct advantages in the treatment of Celiac sprue by the administration of a glutenase when it is desired that the PEP have activity in the upper small intestine. To get to the small intestine, the PEP, if orally administered, must pass through the stomach. If the PEP is degraded or otherwise rendered inactive or less active under gastric conditions, then less PEP activity is available for action in the small intestine, where the physiological conditions are quite different from the stomach with respect to pH, pepsin activity, and other factors.

Figure 1:
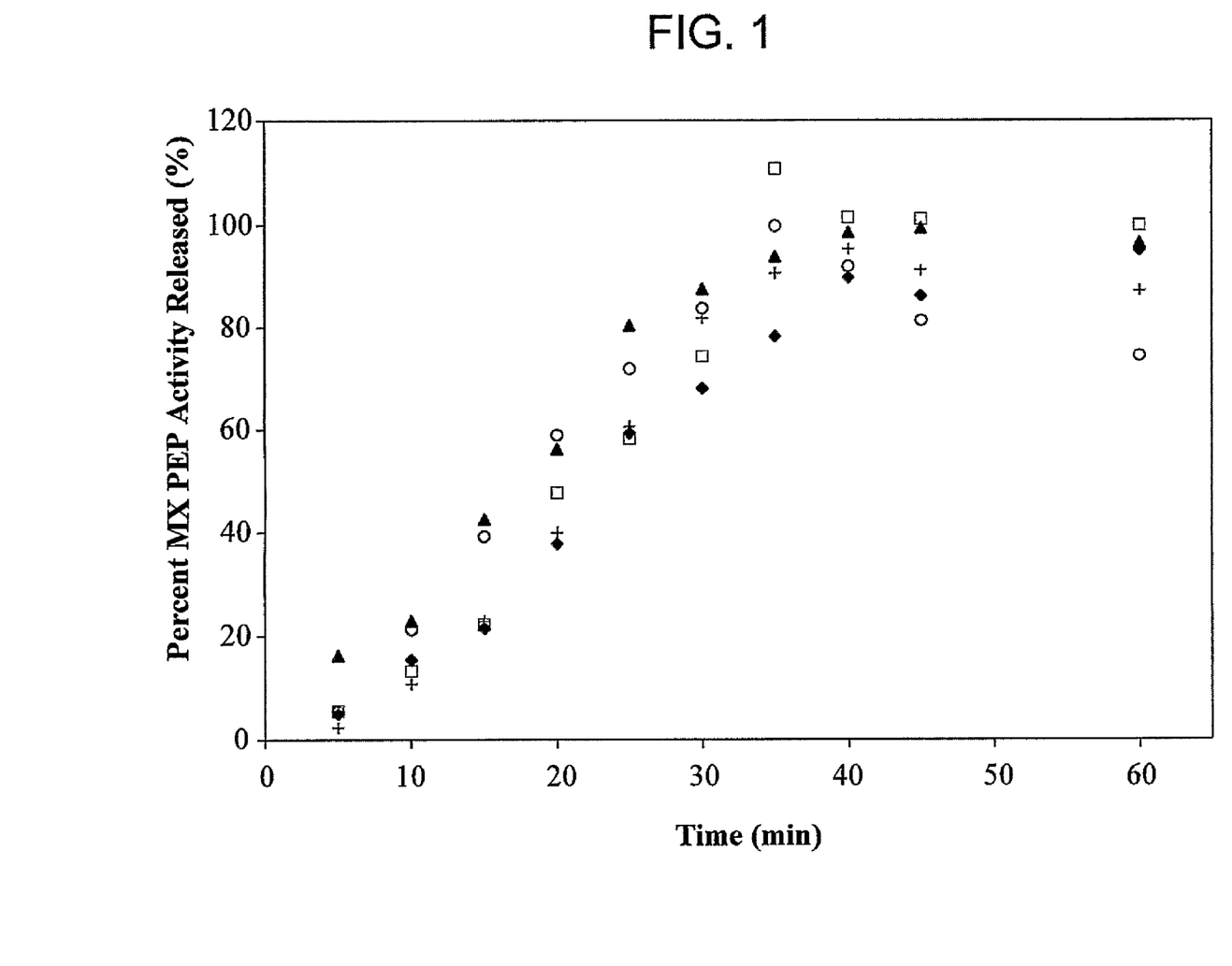
FIG. 1. Activity of MX PEP released from enteric-coated capsules under simulated intestinal conditions.

With reference to the data presented in FIG. 1, the capsule was incubated in the pH 2/pepsin environment for 30 minutes to mimic gastric conditions, and then the pH of the solution was adjusted to 6.0 (a pH in the range typical for small intestine). The activity release of MX PEP enzyme from the capsule in the pH 6.0 environment was determined at various trypsin and chymotrypsin concentrations (0 mg/ml (+), 0.375 mg/ml (▲), 0.75 mg/ml (□), 1.5 mg/ml (♦), and 3.0 mg/ml (○)). Each data point represents an average of two independently prepared capsules, except for the 0.375 mg/ml data points which represent the average of four capsules. All data has been normalized by the theoretical amount of MX PEP activity contained in the capsules.

In addition, FM PEP has been incubated with various levels of the Eudragit enteric coat to demonstrate compatibility of the enzyme with the coating polymer. No enzyme inhibition has been observed for incubations of 30 minutes (at room temperature).

Effect of Pancreatic Proteases and Bile on PEP Stability. Both PEP enzymes have shown remarkable stability versus pancreatic enzymes under in vitro conditions (1 mg/ml trypsin, 1 mg/ml chymotrypsin, 0.2 mg/ml elastase and 0.2 mg/ml carboxypeptidase A in 40 mM phosphate buffer, pH 6.5) (Shan, 2004). However, the stability of both enzymes is significantly decreased in the presence of bile salts and pancreatic enzymes. This has been demonstrated in a variety of experimental systems. The instability of the PEP enzymes under such conditions was shown by incubating the PEP enzymes in intestinal flush samples from Wistar rats. Male Wistar rats were fed a gluten containing meal, euthanized, and the contents from segments of their small intestine (duodenum, jejunum, and ileum) was collected by flushing intestinal segments with saline solution. Both PEPs were inactivated (i.e. less than 5% of initial activity) within 5 minutes of incubating the PEP in the jejunal and ileal flush samples (Table 1). The lack of stability in the rat flush samples was determined to be caused by the presence of bile salts. For example, the stability of the enzyme in the rat flush samples was significantly improved after treating the samples with a bile salt sequestering agent (cholestyramine) in accordance with the teachings of the present invention.

TABLE 1

PEP stablilty in rat intestinal flush samples: The results represent the amount of remaining PEP activity after incubating in the particular rat flush sample at 37° C. for various times. For both cases, the PEP enzyme was incubated in saline solution at 37° C. for the control sample. All results are normalized by the initial activity (time 0) that was measured for that particular incubation.

| Time | FM PEP | | | | MX PEP | | | |
|---|---|---|---|---|---|---|---|---|
| (min) | Control | Duodenum | Jejunum | Ileum | Control | Duodenum | Jejunum | Ileum |
| 0 | 100 | 100 | 100 | 100 | 100 | 100 | 100 | 100 |
| 5 | 66 | 47 | 10 | <5 | 120 | 54 | <5 | <5 |
| 15 | 62 | 8 | <5 | <5 | 142 | 16 | <5 | <5 |
| 30 | 95 | 1 | <5 | <5 | 104 | 3 | <5 | <5 |

Figure 2:
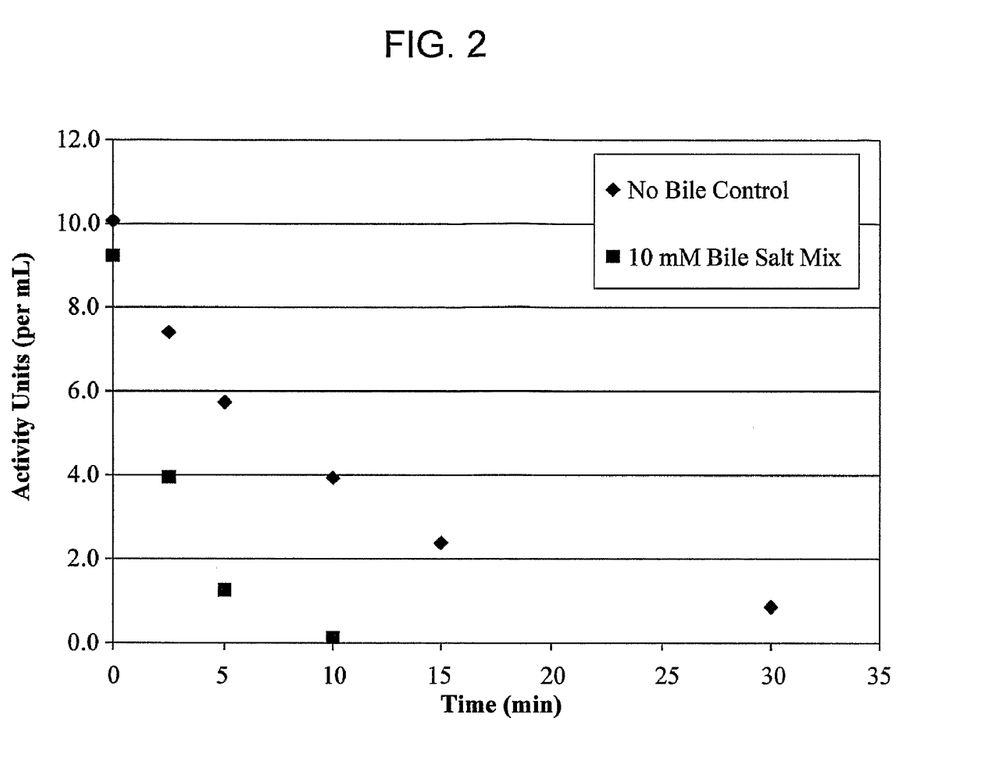
FIG. 2. FM PEP stability in simulated human intestinal solution.

A detailed in vitro evaluation of FM PEP enzyme stability versus bile salts was performed using simulated physiological human bile salt solution (containing 3.2 mM glycochenodeoxycholate, 3.2 mM glycocholate, 1.6 mM glycodeoxycholate, 0.8 mM taurochenodeoxycholate, 0.8 mM taurocholate, and 0.4 mM taurodeoxycholate). FM PEP was incubated at 37° C. in the presence of 15 mg/ml gluten with and without bile with various levels of pancreatic enzymes. The residual activity of FM PEP was measured as a function of time using a chromogenic substrate. These results confirmed the results of the previous experiments, demonstrated that the presence of bile reduces the stability of the FM PEP enzyme. In particular, the instability of FM PEP is triggered by the presence of bile and the pancreatic enzymes (trypsin and chymotrypsin). Bile alone moderately reduces the stability of the FM PEP enzyme, but this effect is magnified by the addition of the pancreatic enzymes (FIG. 2). Thus, in one aspect the present invention provides a variety of methods for determining the stability of a PEP or other glutenase under a variety of physiologically relevant conditions and thereby provides methods for determining the ability of a PEP or other glutenase to detoxify gluten in vivo, particularly in the small intestine but also in the stomach.

With respect to FIG. 2, the results represent the amount of remaining PEP activity after incubating in simulated human intestinal solution at 37° C. for various times. The simulated gluten-containing human intestinal solution contains 10 mM bile, 15 mg/ml gluten, 1 mg/ml trypsin, and 1 mg/ml chymotrypsin.

Figure 3:
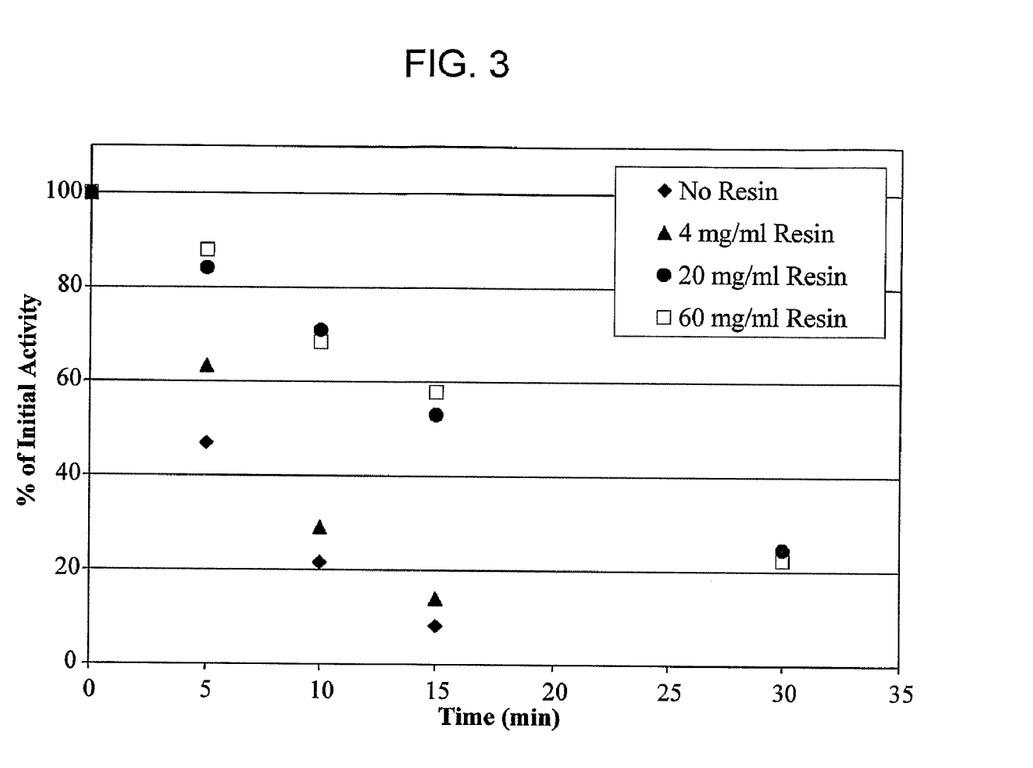
FIG. 3. FM PEP stability in rat intestinal flush sample (jejunal) in the presence of cholestyramine resin.

Protective Effect of Agents that Abolish PEP-Bile Interactions. In accordance with the present invention, the use of cholestyramine, a bile salt sequestering agent, can reduce or eliminate the impact of the bile salts on the activity of the FM PEP enzyme. This was demonstrated in an analogous fashion as the in vitro bile salt incubation, except that a specified amount of cholestyramine resin was added in concert with the FM PEP. This same method can be used in accordance with the invention to test other test agents for ability to stabilize PEP or another glutenase or other protein or peptide under physiologically relevant conditions. Cholestyramine (at levels of approximately 10 mg/ml) eliminated the impact of bile on the FM PEP stability. The protective effect of cholestyramine resin was further confirmed by treating rat intestinal flush samples with the resin and demonstrating an improved stability of the FM PEP enzyme (FIG. 3). The results represent the amount of remaining PEP activity after incubating in the particular rat flush sample at 37° C. for various times. For this demonstration, the same source of rat intestinal flush sample was used for all four cases. The cholestyramine resin was added to the rat intestinal flush sample just prior to the addition of the FM PEP.

EXAMPLE 2

Co-Formulation of Prolyl Endopeptidase and Cholestyramine Resin

A formulation incorporating the cholestyramine resin as an excipient in the lyophilization and formulation process with the PEP enzyme is illustrated in this example. 10-100 mg/ml cholestyramine resin is added directly to a concentrated PEP solution (10 mg/ml) in 50 mM Sodium Phosphate, 3% Sucrose, pH 7.5 buffer. The solution is frozen in a dry ice/ethanol bath and lyophilized to obtain an enzymatically active, easily handled powder. This powder can be coated directly with the Eudragit enteric coat. Alternatively, the cholestyramine resin can be added after the lyophilization process. In this latter process, the cholestyramine resin is blended into the lyophilized product after it is dry.

EXAMPLE 3

Enteric Capsule Formulation of Prolyl Endopeptidase

Gelatin capsules are filled with 100 mg prolyl endopeptidase/cholestyramine resin as described in Example 2, and 10 mg of silicon dioxide. The capsules are enterically coated with Eudragit polymer and put in a vacuum chamber for 72 hours. The capsules can then be held at a range of temperatures for varying amounts of time before loss of PEP activity may render them less useful for their intended purpose. For use in administration in combination with food to Celiac sprue patients, for example, the present invention provides such formulations and unit dose forms of PEPs that are stable at temperatures ranging from 10° C. to 37° C. and at humidity levels of 35-40% for times typical of other orally administered products. Stability testing using controlled temperatures and humidity levels are useful in assessing suitability of a product for a variety of commercial applications.

EXAMPLE 4

Studies of Enteric Capsule Formulation of Prolyl Endopeptidase

A study is conducted where patients with Celiac Sprue are enrolled in a two week-long study. Gelatin capsules provided by the invention containing 90% prolyl endopeptidase/cholestyramine resin as described in Example 2, mixed with 10% silicon dioxide are used. The capsules are hand-filled with the mixture, banded, and coated with a 10% Sureteric enteric coating (a polymer of polyvinylacetatephthalate developed by Colorcon). Samples are acid-tested by exposing the coating to 0.1N HCL for one hour in order to simulate the acid environment of the stomach. The capsules are then put in a vacuum chamber for 72 hours to dry.

Two 100 mg capsules are administered to each patient prior to each meal. In one test method provided by the invention, the Celiac sprue patients are given controlled amounts of gluten, and symptoms of intestinal malabsorbtion, such as high fecal fat content, are measured, or tests for intestinal malabsorption, such as the xylose test, are conducted to determine if the formulation in the amounts administered can prevent the tested amount of gluten from inducing symptoms of active Celiac sprue disease in the patient. In another test, Celiac sprue patients are instructed to eat all kinds of food without abstaining from those that were known to cause distress, e.g., foods that overtly or otherwise contain levels of gluten toxic to the particular patient, and the patient is asked to keep a record of the symptoms of such distress, e.g., bloating, diarrhea, and cramps, to determine if the if the formulation in the amounts administered can prevent or reduce the symptoms of active Celiac sprue disease in the patient.

EXAMPLE 5

Enteric Pill Formulation of Prolyl Endopeptidase 400 mg of L-tartaric acid and 40 mg of polyethylene glycol-hydrogenated castor oil (HCO-60) are dissolved in 5 ml of methanol. This solution is placed in a mortar previously warmed to 30° C. To the solution is added 100 mg of prolyl endopeptidase/cholestyramine resin as described in Example 2. Immediately after the addition of PEP, the mixture is stirred with a pestle under a hot air current (40° C.) and then placed in a desiccator under vacuum overnight to remove the solvent. The resulting solid-mass is pulverized with a pestle and kneaded with 30 mg of sodium bicarbonate and a small amount of 70% ethanol. The mixture is then divided and shaped into pills of about 2 mm size and thoroughly dried. The dried pills are given a coating of hydroxypropylmethylcellulose phthalate (HP-55) to obtain an enteric formulation of the invention. Other formulations of the invention can be made by the appropriate substitution of API.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A pharmaceutical formulation comprising: a glutenase; and
a bile sequestering agent in a dose effective to increase stability of the glutenase.

2. The formulation according to claim 1, wherein said bile sequestering agent is one or more of cholestyramine, colestipol, and colesevelam.

3. The formulation according to claim 1, wherein said glutenase is selected from the group consisting of *Flavobacterium meningosepticum* prolyl endopeptidase (FM PEP), Sphingomonas capsulate prolyl endopeptidase (SC PEP), Myxococcus xanthus prolyl endopeptidase (MX prolyl endopeptidase) and barley EP-B2 endoproteinase.

4. The formulation according to claim 3, wherein said glutenase comprises two or more of MX PEP; SC PEP; FM PEP; and barley EP-B2 endoproteinase.

5. The formulation according to any of claims 1-2 or 3, wherein said formulation comprises an enteric coating.

6. The formulation of claim 1, wherein the bile sequestering agent is present as a unit dose of at least 0.5 g.

* * * * *